US008377042B2

(12) United States Patent
Li et al.

(10) Patent No.: US 8,377,042 B2
(45) Date of Patent: Feb. 19, 2013

(54) OPHTHALMIC DEVICES FOR THE CONTROLLED RELEASE OF ACTIVE AGENTS

(75) Inventors: Zhigang Li, Hillsborough, NJ (US); Michael J. Trezza, II, Long Valley, NJ (US); Maureen J. Borgia, Somerville, NJ (US); Aruna Nathan, Bridgewater, NJ (US); Bret A. Coldren, Vista, CA (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 12/779,238

(22) Filed: May 13, 2010

(65) Prior Publication Data

US 2011/0022007 A1 Jan. 27, 2011

Related U.S. Application Data

(63) Continuation of application No. 12/437,163, filed on May 7, 2009, now abandoned.

(60) Provisional application No. 61/051,085, filed on May 7, 2008.

(51) Int. Cl.
A61K 9/22 (2006.01)

(52) U.S. Cl. .................................... 604/890.1

(58) Field of Classification Search ................... 424/427; 427/2.21, 2.22; 604/890.1, 891.1, 244, 294
See application file for complete search history.

(56) References Cited

U.S. PATENT DOCUMENTS

| | | | |
|---|---|---|---|
| 5,962,548 A | 10/1999 | Vanderlaan et al. | |
| 6,020,445 A | 2/2000 | Vanderlaan et al. | |
| 6,099,852 A | 8/2000 | Jen | |
| 6,196,993 B1* | 3/2001 | Cohan et al. ............... | 604/891.1 |
| 6,367,929 B1 | 4/2002 | Maiden et al. | |
| 6,565,535 B2* | 5/2003 | Zaias et al. ................. | 604/152 |
| 6,822,016 B2 | 11/2004 | McCabe et al. | |
| 2003/0018306 A1* | 1/2003 | Bucay-Couto et al. ...... | 604/265 |

FOREIGN PATENT DOCUMENTS

| | | |
|---|---|---|
| WO | 0062760 A1 | 10/2000 |
| WO | 2006031658 A2 | 3/2006 |
| WO | 2006031658 A3 | 4/2006 |
| WO | 2007149771 A2 | 12/2007 |
| WO | 2007149771 A3 | 2/2008 |

OTHER PUBLICATIONS

PCT International Search Report . PCT/2009/043139 date of mailing Sep. 15, 2009.

* cited by examiner

*Primary Examiner* — Victoria P Shumate
(74) *Attorney, Agent, or Firm* — Wayne C. Jaeschke, Jr.

(57) ABSTRACT

The invention provides devices useful for the delivery of active agents to the eye in a controlled manner. In the devices of the invention, the active agent is present within the device in a continuous or discontinuous concentration gradient.

16 Claims, 9 Drawing Sheets

OPHTHALMIC DEVICES FOR THE CONTROLLED RELEASE OF ACTIVE AGENTS

CROSS REFERENCE TO RELATED APPLICATIONS

This application is a continuation of U.S. patent application Ser. No. 12/437,163, filed May 7, 2009 now abandoned which claims priority to U.S. Provisional patent application Ser. No. 61/051,085, filed May 7, 2008; both of which are hereby incorporated by reference in their entireties.

FIELD OF THE INVENTION

The present invention relates to devices suitable for delivering substances to one or more of the eye, nose and throat. In particular, the invention relates to devices capable of delivering one or more active agents in a controlled manner over a period time.

BACKGROUND OF THE INVENTION

Active agents frequently are administered to the eye for the treatment of ocular diseases and disorders. Conventional means for delivering active agents to the eye involve topical application to the surface of the eye. The eye is uniquely suited to topical administration because, when properly constituted, topically applied active agents can penetrate through the cornea and rise to therapeutic concentration levels inside the eye. Active agents for ocular diseases and disorders may be administered orally or by injection, but such administration routes are disadvantageous in that, in oral administration, the active agent may reach the eye in too low a concentration to have the desired pharmacological effect and their use is complicated by significant, systemic side effects and injections pose the risk of infection.

The majority of ocular active agents are currently delivered topically using eye drops which, though effective for some applications, are inefficient. When a drop of liquid is added to the eye, it overfills the conjunctival sac, the pocket between the eye and the lids, causing a substantial portion of the drop to be lost due to overflow of the lid margin onto the cheek. In addition, a substantial portion of the drop that remains on the ocular surface is drained into the lacrimal puncta, diluting the concentration of the drug.

It is known to use devices that may be inserted into one or more of an orifice of an individual's eye, such as a lacimal punctum, to deliver active agents. One disadvantage of using such devices to deliver agents is that much of the agent may delivered in an initial, large bolus upon insertion of the device into the eye rather than a more linear delivery of the agent over time.

DETAILED DESCRIPTION OF THE INVENTION AND ILLUSTRATIVE EMBODIMENTS

Figure 1:
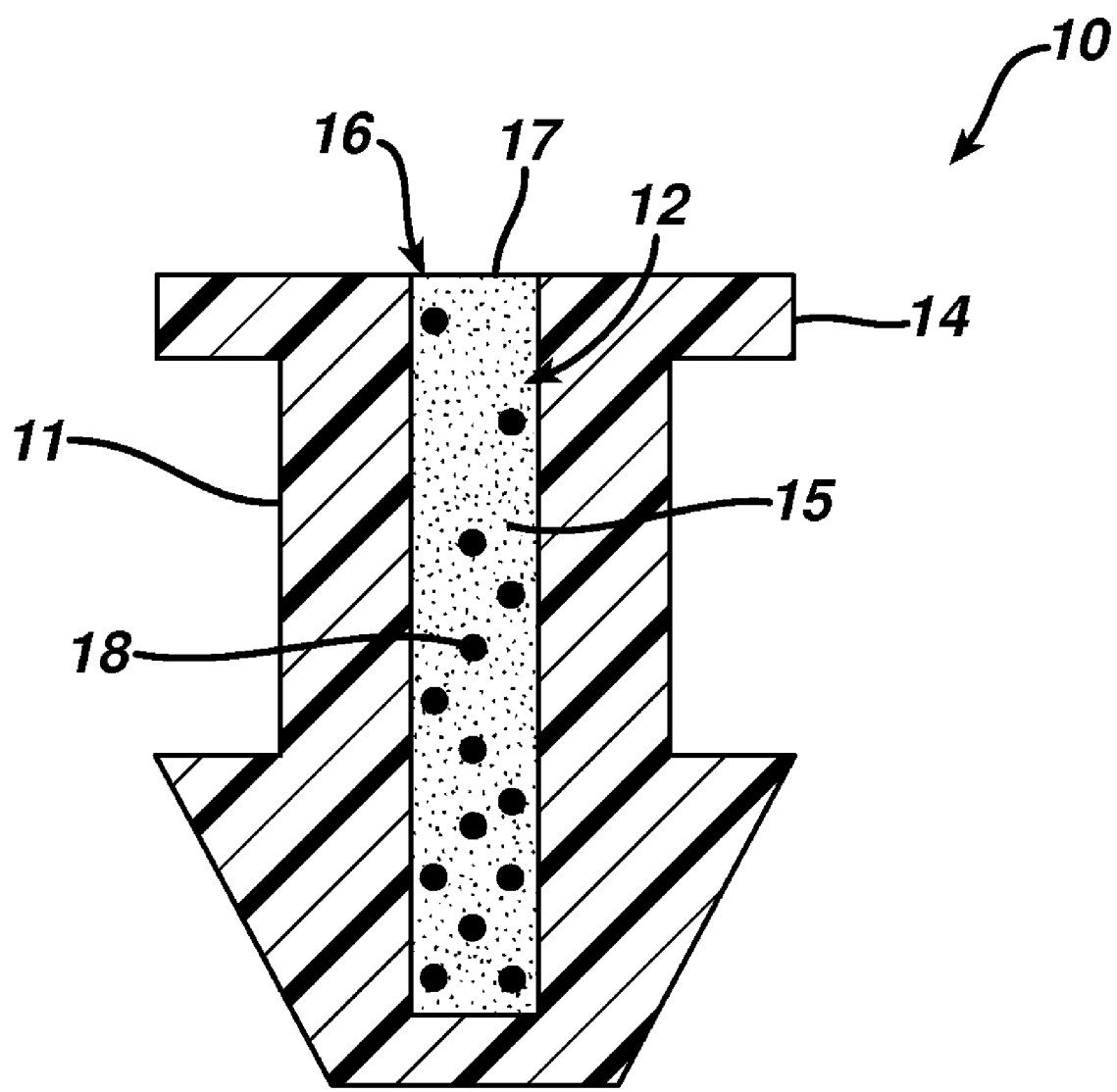
FIG. 1 is a first embodiment of the invention.

The present invention provides devices, and methods for their manufacture, that can be used to deliver active agents to the eye in a controlled manner. Thus, in one embodiment, the invention comprises an ophthalmic device comprising, consisting essentially of, and consisting of: a body having a first end and a second end; a surface extending between the two ends; a reservoir contained within the body wherein the reservoir comprises, consists essentially of, and consists of at least one opening, an active agent-containing material and an active agent, wherein the active agent is present in a continuous or discontinuous concentration gradient within the active agent-containing material.

In a preferred embodiment, the invention provides punctal plugs that may be used to deliver active agents to one or both of the nasolacrimal duct and to the tear fluid of the eye. This embodiment provides a punctal plug comprising, consisting essentially of, and consisting of: a body having a first end and a second end; a surface extending between the two ends; a reservoir contained within the body wherein the reservoir comprises, consists essentially of and consists of at least one opening, an active agent-containing material and an active agent, wherein the active agent is present in a continuous or discontinous concentration gradient within the active agent-containing material.

As used herein, the term "active agent" refers to an agent capable of treating, inhibiting, or preventing a disorder or a disease. Exemplary active agents include, without limitation, pharmaceuticals and nutraceuticals. Preferred active agents are capable of treating, inhibiting, or preventing a disorder or a disease of one or more of the eye, nose and throat.

As used herein, the term "punctal plug" refers to a device of a size and shape suitable for insertion into the inferior or superior lacrimal canaliculus of the eye through, respectively, the inferior or superior lacrimal punctum.

As used herein, the term "opening" refers to an opening in the body of a device of the invention of a size and shape through which the active agent can pass. Preferably, only the active agent can pass through the opening. The opening may be covered with a membrane, mesh, grid or it may be uncovered. The membrane, mesh, or grid may be one or more of porous, semi-porous, permeable, semi-permeable, and biodegradable.

The devices of the invention have a reservoir in which is found an active agent-containing material and an active agent therein. The active agent may be dispersed throughout the active agent-containing material or dissolved within the material. Alternatively, the active agent may be contained in inclusions, particulates, droplets, or micro-encapsulated within the material. Still as another alternative, the active agent may be covalently bonded to the material and released by hydrolysis, enzymatic degradation and the like. Yet as another alternative, the active agent may be in a reservoir within the material.

It is a discovery of the invention that the active agent may be released in a controlled manner, meaning over a period of time by using an active agent-containing material in which the agent is present in a continuous concentration gradient throughout the material or by using a discontinuous concentration gradient. This is in contrast to a device that exhibits a "burst" or immediate release upon insertion of an amount of active agent that is greater than the average release rate over time.

Without being bound to any particular theory, it is believed that an active agent-containing material that does not undergo significant chemical degradation during the time desired for the release of active agent will release the agent by diffusion through the matrix to a device's release surfaces, meaning surfaces of the active agent-containing material in contact with a person's body fluid. According to Fick's Law, the diffusive transport or flux, J, of the agent through the active agent-containing material is governed at each point and each time by the local concentration gradient, the diffusivity of the active agent with the material D, and the spatial variation of the cross-sectional geometry of the device.

The local gradient may be controlled by placing more active agent at one location in the active agent-containing material relative to another location. For example, the concentration profile can be a continuous gradient from one end of the material to the other. Alternatively, the matrix may be have a discontinuous gradient, meaning that one section of the material has a first concentration and the concentration abruptly changes to a second, different concentration in an adjacent section of the matrix. The diffusivity for the active agent may also be spatially controlled by varying one or more of the chemical composition, porosity, and crystallinity of the active agent-containing material Additionally, the spatial variation of the material's cross-sectional geometry may be used to control diffusivity. For example, if the material was in the form of a straight rod that has a uniform active agent concentration, diffusivity will be reduced when the area at the open end of the material is significantly smaller than the average of the entire material. Preferably, the material area at the open end of the device is no more than one-half of the average cross sectional area of the material, meaning the cross section determined perpendicular to the primary dimension of active agent transport use.

One of ordinary skill in the art will recognize that, depending on how one varies one or more of the local concentration gradient, the diffusivity of the active agent from the material D, and the spatial variation of the cross-sectional geometry of the device, a variety of release profiles may be obtained including, without limitation first order, second order, biphasic, pulsatile and the like. For example, either or both of the active agent concentration and diffusivity may increase from the surface to the center of the active agent-containing material in order to achieve more initial release. Alternatively, either or both may be increased or decreased and then increased again within the material to achieve a pulsatile release profile. The ability to achieve a variety of release profiles by varying local concentration gradient, the diffusivity of the active agent, and the spatial variation of the cross-sectional geometry may eliminate the need for rate-limiting membranes in the device.

The devices of the invention contain a reservoir within the body, and the reservoir contains at least one active agent-containing material. The body is preferably impermeable to the active agent, meaning only an insubstantial amount of active agent can pass therethrough, and the body has at least one opening through which the active agent is released. The active agent-containing material useful in the devices of the invention is any material that is capable of containing the active agent, does not alter the chemical characteristics of the active agent, and does not significantly chemically degrade or physically dissolve when placed in contact with ocular fluids. Preferably, the active agent-containing material is non-biodegradable, meaning that it does not degrade to a substantial degree upon exposure to biologically active substances typically present in mammals. Additionally, the active agent-containing material is capable of releasing the active agent by one or more of diffusion, degradation, or hydrolyzation. Preferably, the active agent-containing material is a polymeric material, meaning that it is a material made of one or more types of polymers.

When the active agent-containing material is combined with the active agent, the material may also contain one or more materials that are insoluble in water and non-biodegradable, but from which the active agent can diffuse. For example, if the active agent-containing material is a polymeric material, the material may be composed of one or more polymers that are insoluble in water and non-biodegradable.

Suitable polymeric materials for the active agent-containing material include, without limitation, hydrophobic and hydrophilic absorbable and non-absorbable polymers. Suitable hydrophobic, non-absorbable polymers include, without limitation, ethylene vinyl alcohol ("EVA"), fluorinated polymers including without limitation, polytetrafluoroethylene ("PTFE") and polyvinylidene fluoride ("PVDF"), polypropylene, polyethylene, polyisobutylene, nylon, polyurethanes, polyacrylates and methacrylates, polyvinyl palmitate, polyvinyl stearates, polyvinyl myristate, cyanoacrylates, epoxies, silicones, copolymers thereof with hydrophobic or hydrophilic monomers, and blends thereof with hydrophilic or hydrophobic polymers and excipients.

Hydrophilic, non-absorbable polymers useful in the invention include, without limitation, cross-linked poly(ethylene glycol), poly(ethylene oxide), polypropylene glycol), poly (vinyl alcohol), poly(hydroxyethyl acrylate or methacrylate), poly(vinylpyrrolidone), polyacrylic acid, poly(ethyloxazoline), and poly(dimethyl acrylamide), copolymers thereof with hydrophobic or hydrophilic monomers, and blends thereof with hydrophilic or hydrophobic polymers and excipients.

Hydrophobic, absorbable polymers that may be used include, without limitation, aliphatic polyesters, polyesters derived from fatty acids, poly(amino acids), poly(ether-esters), poly(ester amides), polyalkylene oxalates, polyamides, poly(iminocarbonates), polycarbonates, polyorthoesteres, polyoxaesters, polyamidoesters, polyoxaesters containing amine groups, phosphoesters, poly)anhydrides), polypropylene fumarates, polyphosphazenes, and blends thereof. Examples of useful hydrophilic, absorbable polymers include, without limitation, polysaccharides and carbohydrates including, without limitation, crosslinked alginate, hyaluronic acid, dextran, pectin, hydroxyethyl cellulose, hydroxy propyl cellulose, gellan gum, guar gum, keratin sulfate, chondroitin sulfate, dermatan sulfate, proteins including, without limitation, collagen, gelatin, fibrin, albumin and ovalbumin, and phospholipids including, without limitation, phosphoryl choline derivatives and polysulfobetains.

More preferably, the active agent-containing material is a polymeric material that is polycaprolactone. Still more preferably, the material is poly(epsilon-caprolactone), and ethylene vinyl acetate of molecular weights between about 10,000 and 80,0000. About 0 to about 100 weight percent polycaprolactone and about 100 to about 0 weight percent of the ethylene vinyl acetate are used based on the total weight of the polymeric material and, preferably, about 50% each of polycaprolactone and ethylene vinyl acetate is used.

The polymeric material used is preferably greater than about 99% pure and the active agents are preferably greater than about 97% pure. One of ordinary skill in the art will recognize that in compounding, the conditions under which compounding is carried out will need to take into account the characteristics of the active agent to ensure that the active agents do not become degraded by the process. The polycaprolactone and ethylene vinyl acetate preferably are combined with the desired active agent or agents, micro-compounded, and then extruded.

In a preferred embodiment, the active agent-containing material is a polymeric material that is combined with at least one active agent to form one or more fiber or fiber-like structures, the dimensions of the fiber which may be substantially the dimensions of the reservoir or smaller than such dimensions. One or more of the fibers or fiber-like structures may be inserted into the reservoir through the opening in the body and, thus, the fibers or fiber-like structures may be of a size and a shape suitable for insertion into the opening. In embodiments in which the device is a punctal plug, the fibers or fiber-like structures preferably are about 0.5 to about 5 mm in length and 0.05 to about 2 mm in diameter. More preferably, the dimensions of the fibers are such that the fibers fit securely into the reservoir and remains in the reservoir when the device is in use in a wearer's eye. In any of the devices of the invention, the fibers may be symmetrical or asymmetrical, depending upon the shape of the reservoir. The internal walls of the reservoir may be substantially smooth or may include features that aid in maintaining the fiber within the reservoir including, without limitation, surfaces with grooves, indentations, roughness or the like in the interior walls.

Alternatively, the fibers containing the active agent or agents may be formed and the device cast around the fibers. As yet another alternative, the fibers and active agent may be dosed into the plug reservoir as a melt and allowed to solidify. As still another alternative, the polymer and active agent may be introduced as a solution. The solution may contain monomers, pre-polymers and the like suitable for cross-linking via one or more of irradiation, redox, and thermal radical polymerization. As yet another alternative, the fibers may simply be soaked in the active agent before or after insertion in the device. In the case in which more than one fiber is used, each of the fibers can have a different cross-sectional shape or diameter than one or more of the other fibers.

Referring to FIG. 1, a device that is a punctal plug 10 of the invention is shown. Plug 10 has body 11 with a reservoir 12 therein that contains at least one opening 16. For purposes of the invention, the bottom of the plug is the portion of the plug inserted first into the lacrimal canaliculus on insertion and the top portion is the opposite end of the plug. Optionally and preferably, and as shown, the bottom of the plug will include an enlarged portion. Also optionally and preferably and as shown, the top portion may include a collarette 14. The collarette is a portion of the punctal plug that extends radially outwardly from one end of the body to a degree sufficient, and having a size and a shape, such that at least a portion of the collarette will extend beyond and be exterior to the lacrimal punctum after insertion of the punctal plug into the lacrimal canaliculus. Typically, the collarette will extend about 0.2 to about 1 mm beyond the plug body. The portion of the punctal plug below the collarette is inserted into one of the inferior lacrimal punctum or the superior lacrimal punctum. The enlarged portion and collarette facilitate the top of the plug remaining at or above the opening of the canaliculus on insertion. If the punctal plugs are being used to deliver active agent to the nasolacrimal duct, the punctal plugs may not have a collarette so that they may be inserted at a sufficient depth within one or both of the lacrimal canaliculi such that the active agent is released into the lacrimal sac.

Active agent 18 is contained within active agent-containing material 15 and release surface 17 is shown. As depicted, active agent-containing material 15 contains a gradient of active agent with the highest concentration of the active agent located at the bottom of the reservoir, meaning the portion of the reservoir located at or near the bottom of the plug. The concentration gradually and continuously increases within the active agent-containing material as one moves from the release surface located at the top of plug 10 toward the bottom of the plug.

In the embodiments in which there is a discontinuous gradient used, the discontinuous gradient may be formed in any convenient manner. For example, more than one active agent-containing material may be used. In this embodiment, each of the active agent-containing materials may be made from the same or different material as each of the other materials and may be the same size and shape or of a different size and shape than one or more of the other materials. The concentrations of active agent in each of the materials may, and preferably will, differ from each other, but there must be an abrupt change in concentration as one moves from one active agent-containing material to another. Alternatively, the active agent concentration may abruptly vary within the same active agent-containing material. For example, a first area of a material may have a high concentration, another and adjacent area of the same material may have a lower concentration, and a third area, adjacent to only the second area may have a concentration higher than that of the second area. Preferably, the difference in concentration will be about 5%, more preferably 25%, and most preferably 50%.

Figure 2:
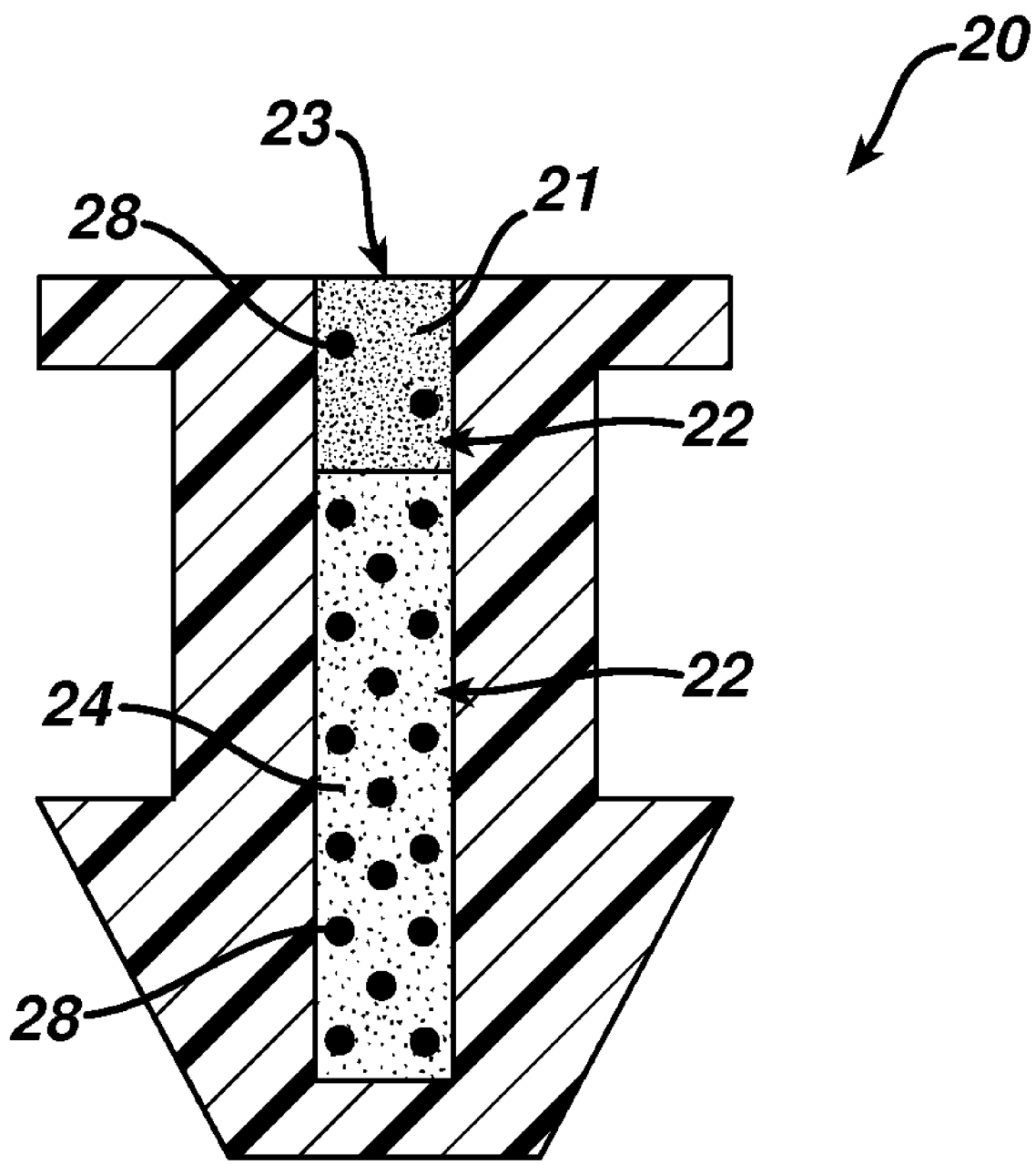
FIG. 2 is a second embodiment of the invention.

In FIG. 2 is shown a second embodiment of the invention in which there is a discontinuous gradient. As depicted, punctal plug 20 has reservoir 22 with an opening 23 therein. A first active agent-containing material 21 containing active agent 28 in a first concentration is located at the topmost portion of the reservoir and a second active agent-containing material 24 containing the active agent 28 in a second concentration, higher than that of the first material 21, is provided in the bottom portion of reservoir 22.

In embodiments of the invention in which there is a discontinuous gradient, more than one active agent may used. For example, the first active agent-containing material may have an active agent therein that differs from the active agent within the second active agent-containing material.

Figure 3:
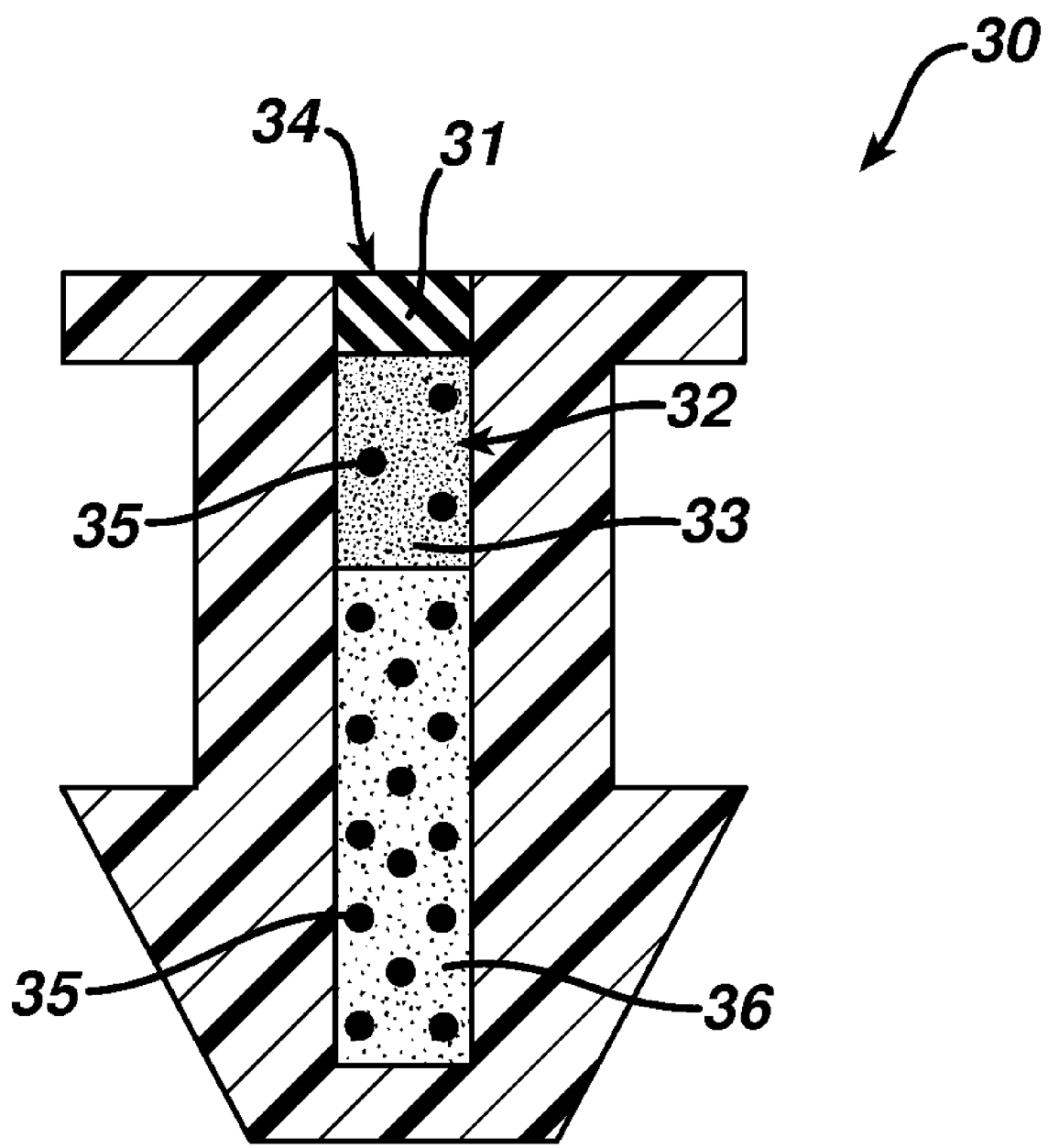
FIG. 3 is a third embodiment of the invention.

In the devices of the invention, a release-modulating component may be included. The release-modulating component may be any component that acts to modulate the release of the active agent from the plug. Suitable modulating component include, without limitation, one or more biodegradable of non-biodegradable semi-permeable membrane, one or more pores, or combinations thereof. In FIG. 3 is shown a third embodiment of the invention in which there is a discontinuous gradient and a modulating component. As depicted, punctal plug 30 has reservoir 32 with an opening 34 therein. A first active agent-containing material 33 containing active agent 35 in a first concentration is located at the topmost portion of the reservoir and a second active agent-containing material 36 containing the active agent 35 in a second concentration is provided in the bottom portion of reservoir 32. Membrane 31, which is located adjacent to and, with respect to the top of plug 30, superior to first active agent-containing material 33 is shown. In a more preferred embodiment, in addition to a gradient, release of the active agent is controlled by use of one or both of active agent loading and release enhancers.

In the discontinuous gradient embodiments of in the invention, two or more fiber sections may be melted or otherwise adhered together. This offers the advantage of mechanical stability of the fiber sections and consistent diffusive contact during manufacture and throughout use of the drug delivery device. The fibers may be melted or adhered together by any convenient method. For example, one poly(epsilon-caprolactone) and ethylene vinyl acetate fiber having a length of about 0.75 to about 1.25 mm with an active agent concentration of about 50 percent by weight may be inserted into a punctal plug. A second poly(epsilon-caprolactone) and ethylene vinyl acetate fiber having a length of about 1.25 to about 1.75 mm and a drug concentration of about 35% is subsequently inserted into the plug so that it rests on top of the first fiber. The plug is then placed in an oven and heated at a temperature between about 57 to 62° C. for about 60 seconds In addition to or instead of active agent loading profiles, the release kinetics may be controlled via spatial gradients of the properties of degradability and drug permeability of the active agent-containing material. For example, in those cases in which drug release kinetics are dominated by the rate of material degradation, a spatial degradation in the material chemistry including, without limitation, polylactide-glycolide copolymers of differing monomer ratios, adjacent polyglycolide and polycaprolactone layers and the like, results in spatial gradients and varied release rates as the material degradation front moves through the device. By way of further example, a material may erode more slowly initially in a first, outer material and more quickly in a second, inner material to achieve phased release kinetics.

In the case of a non-degradable material that elutes the active agent solely through diffusion-dominated mechanisms, spatial gradients in the material's permeability can control release kinetics beyond what is possible with a homogeneous material. In the diffusion-dominated mechanism, the material permeability controls release kinetics and is influenced by the material's porosity as well as the active agent solubility and diffusivity. By forming an active agent-loaded layer of an outer material with a higher permeability, the active agent elution may be controlled to be more linear with less burst effect than that which is otherwise achieved with a single, homogeneous, diffusion material.

The spatial gradients in biodegradability or permeability may be combined with continuous or step-wise gradients in the active agent loading profile. For example, a punctal plug material core having an outer segment loaded with a low active agent concentration and with a relatively low active agent permeability may be adjacent to an inner material segment loaded with a high agent concentration and with a relatively high active agent permeability, which combination achieves release kinetics unobtainable with a homogeneous material ad homogeneous active agent loading. The initial burst release is reduced and the release of the last active agent content is accelerated relative to a conventional homogeneous active agent loaded device.

Phase-separated inclusions may be used to control one or both of diffusive and degradative kinetics of the active agent-containing material. For example, water soluble polymers, water soluble salts, materials with a high diffusivity for the active agent and the like may be used as destabilizing inclusion to enhance degradation or diffusion rates. When the hydrolysis front reaches an inclusion, the inclusion rapidly dissolves and increases porosity of the active agent-containing material. The inclusions may be incorporated as gradients or layers that allow additional tailoring of the release profile.

As another alternative, a percolated network of destabilizing inclusions may be used. When used in a non-biodegradable active agent-containing material, these inclusions form islands within the material that can possess high diffusivity for the active agent. Useful inclusions will have a higher diffusivity for the active agent than the active agent-containing material. Examples of such inclusions include, without limitation, propylene glycol, silicone oil, immiscible dispersed solids such as a polymer or wax and the like. As yet another example, an inclusion that acts to adsorb water, swell the active agent-containing material and increase local diffusion kinetics may be used.

As still another alternative, stabilizing inclusions that have a low active agent diffusivity are used. These inclusions act to form a barrier that slows diffusive transport of the active agent in the vicinity of the inclusion. The overall effect is a reduction of active agent permeability in a base material that is otherwise the same. Example of such inclusions include, without limitation, micro to nano-sized silicate particles dispersed through the base material of one or both of polycaprolactone and ethylenecovinylacetate homogeneously or in continuous step-wise gradients.

The present invention encompasses numerous devices for the delivery of active agents to the eye each having various features and advantages. For example, certain devices may have a body with a first end, a second end, and a lateral surface extending between the two ends. The lateral surface preferably has an outer diameter that is substantially circular in shape and, thus, the body preferably has a cylindrical shape. A portion of the lateral surface of certain of the devices preferably has an outer diameter that is greater than the outer diameter of the remainder of the lateral surface as shown in FIG. 1. The enlarged portion can be any size or shape, and can be present on any part of the lateral surface, In punctal plug embodiments, the enlarged portion is of a size so that it at least partially anchors the punctal plug in the lacrimal canaliculus and preferably, the enlarged portion is at one end of the plug. Conveniently, the enlarged portion may take the shape of an inverted triangle having a flattened apex, as shown in FIG. 1, may have an untapered, body rounded at the end, or may have a tapered shape at one end with a rounded point as shown in FIG. 10. One ordinarily skilled in the art will recognize that any of a wide variety of shapes are possible.

The body of the punctal plugs of the invention may take any shape and size, Preferably, the body is in the shape of an elongated cylinder. The body will be about 0.8 to about 5 mm in length, preferably about 1.2 to about 2.5 mm in length. The width of the body will be about 0.2 to about 3, preferably 0.3 to about 1.5 mm. The size of the opening will be from about 1 nm to about 2.5 mm and preferably about 0.15 mm to about 0.8 mm. Instead of one large opening at any one location, multiple small openings may be used. The body of the plug may be wholly or partially transparent or opaque. Optionally, the body may include a tint or pigment that makes the plug easier to see when it is placed in a punctum.

The body of the devices of the invention may be made of any suitable biocompatible material including, without limitation, silicone, silicone blends, silicone co-polymers, such as, for example, hydrophilic monomers of polyhydroxyethylmethacrylate ("pHEMA"), polyethylene glycol, polyvinylpyrrolidone, and glycerol, and silicone hydrogel polymers such as, for example, those described in U.S. Pat. Nos. 5,962, 548, 6,020,445, 6,099,852, 6,367,929, and 6,822,016, incorporated herein in their entireties by reference. Other suitable biocompatible materials include, for example: polyurethane; polymethylmethacrylate; poly(ethylene glycol); poly(ethylene oxide); poly(propylene glycol); poly(vinyl alcohol); poly (hydroxyethyl methacrylate); poly(vinylpyrrolidone) ("PVP"); polyacrylic acid; poly(ethyloxazoline); poly(dimethyl acrylamide); phospholipids, such as, for example, phosphoryl choline derivatives; polysulfobetains; acrylic esters, polysaccharides and carbohydrates, such as, for example, hyaluronic acid, dextran, hydroxyethyl cellulose, hydroxyl propyl cellulose, gellan gum, guar gum, heparan sulfate, chondritin sulfate, heparin, and alginate; proteins such as, for example, gelatin, collagen, albumin, and ovalbumin; polyamino acids; fluorinated polymers, such as, for example, PTFE, PVDF, and teflon; polypropylene; polyethylene; nylon; and EVA.

The surface of the devices may be wholly or partially coated. The coating may provide one or more of lubriciousness to aid insertion, muco-adhesiveness to improve tissue compatibility, and texture to aid in anchoring the device. Examples of suitable coatings include, without limitation, gelatin, collagen, hydroxyethyl methacrylate, PVP, PEG, heparin, chondroitin sulphate, hyaluronic acid, synthetic and natural proteins, and polysaccharides, thiomers, thiolated derivatives of polyacrylic acid and chitosan, polyacrylic acid, carboxymethyl cellulose and the like and combinations thereof.

Certain embodiments of the devices of the invention have a body made of a flexible material that conforms to the shape of whatever it contacts. Optionally, in the punctal plug embodiment, there may be a collarette formed of either a less flexible material than that of the body or material that too conforms to the shape of whatever it contacts. When a punctal plug having both a flexible body and a less flexible collarette is inserted into the lacrimal canaliculus, the collarette rests on the exterior of the lacrimal punctum and the body of the punctal plug conforms to the shape of the lacrimal canaliculus. The reservoir and the body of such punctal plugs are preferably coterminous. That is, the reservoir of such punctal plugs preferably make up the entirety of the body, except for the collarette.

In embodiments in which one or both of a flexible body and collarette are used, the flexible body and flexible collarette can be made of materials that include, without limitation, nylon, polyethylene terephthalate ("PET"), polybutlylene terephthalate ("PBT"), polyethylene, polyurethane, silicone, PTFE, PVDF, and polyolefins. Punctal plugs made of nylon, PET, PBT, polyethylene, PVDF, or polyolefins are typically manufactured for example and without limitation, extrusion, injection molding, or thermoforming. Punctal plugs made of latex, polyurethane, silicone, or PTFE are typically manufactured using solution-casting processes.

Processes for manufacturing the devices useful in the invention are well known. Typically, the devices are manufactured by injection molding, cast molding, transfer molding or the like. Preferably, the reservoir is filled with one or both of at least one active agent and the active agent-containing material subsequent to the manufacture of the device. Additionally, one or more excipients may be combined with the active agent alone or in combination with the polymeric material.

The amount of active agent used in the devices of the invention will depend upon the active agent or agents selected, the desired doses to be delivered via the device, the desired release rate, and the melting points of the active agent and active agent-containing material. Preferably, the amount used is a therapeutically effective amount meaning an amount effective to achieve the desired treatment, inhibitory, or prevention effect. Typically, amounts of about 0.05 to about 8,000 micrograms of active agents may be used.

In certain aspects of the invention, the reservoir can be refilled with a material after substantially all of the active agent-containing material has dissolved or degraded and the active agent is released. For example, the new active agent-containing material can be the same as, or different from, the previous polymeric material, and can contain at least one active agent that is the same as, or different from the previous active agent. Certain punctal plugs used for particular applications can preferably be refilled with a material while the punctal plugs remain inserted in the lacrimal canaliculus, while other punctal plugs are typically removed from the lacrimal canaliculus, a new material is added, and the punctal plugs are then reinserted into the lacrimal canaliculus.

After the device is filled with the active agent, the plug is sterilized by any convenient method including, without limitation, ethylene oxide, autoclaving, irradiation, and the like and combination thereof. Preferably, sterilization is carried out through gamma radiation or use of ethylene oxide.

The devices described herein can be used to deliver various active agents for the one or more of the treatment, inhibition, and prevention of numerous diseases and disorders. Each device may be used to deliver at least one active agent and can be used to deliver different types of active agents. For example, the devices can be used to deliver azelastine HCl, emadastine difumerate, epinastine HCl, ketotifen fumerate, levocabastine HCl, olopatadine HCl, pheniramine maleate, and antazoline phosphate for one or more of the treatment, inhibition, and prevention of allergies. The devices can be used to deliver mast cell stabilizers, such as, for example, cromolyn sodium, lodoxamide tromethamine, nedocromil sodium, and permirolast potassium.

The devices can be used to deliver mydriatics and cycloplegics including, without limitation, atropine sulfate, homatropine, scopolamine HBr, cyclopentolate HCl, tropicamide, and phenylephrine HCl. The devices can be used to deliver ophthalmic dyes including, without limitation, rose begal, sissamine green, indocyanine green, fluorexon, and fluorescein.

The devices can be used to deliver corticosteroids including, without limitation, dexamethasone sodium phosphate, dexamethasone, fluoromethalone, fluoromethalone acetate, loteprednol etabonate, prednisolone acetate, prednisolone sodium phosphate, medrysone, rimexolone, and fluocinolone acetonide. The devices can be used to deliver non-steroidal anti-inflammatory agents including, without limitation, flurbiprofen sodium, suprofen, diclofenac sodium, ketorolac tromethamine, cyclosporine, rapamycin methotrexate, azathioprine, and bromocriptine.

The devices can be used to deliver anti-infective agents including, without limitation, tobramycin, moxifloxacin, ofloxacin, gatifloxacin, ciprofloxacin, gentamicin, sulfisoxazolone diolamine, sodium sulfacetamide, vancomycin, polymyxin B, amikacin, norfloxacin, levofloxacin, sulfisoxazole diolamine, sodium sulfacetamide tetracycline, doxycycline, dicloxacillin, cephalexin, amoxicillin/clavulante, ceftriaxone, cefixime, erythromycin, ofloxacin, azithromycin, gentamycin, sulfadiazine, and pyrimethamine.

The devices can be used to deliver agents for the one or more of the treatment, inhibition, and prevention of glaucoma including, without limitation, epinephrines, including, for example: dipivefrin; alpha-2 adrenergic receptors, including, for example, aproclonidine and brimonidine; betablockers including, without limitation, betaxolol, carteolol, levobunolol, metipranolol, and timolol; direct miotics, including, for example, carbachol and pilocarpine; cholinesterase inhibitors, including, without limitation, physostigmine and echothiophate; carbonic anhydrase inhibitors, including, for example, acetazolamide, brinzolamide, dorzolamide, and methazolamide; prostoglandins and prostamides including, without limitation, latanoprost, bimatoprost, uravoprost, and unoprostone cidofovir.

The devices can be used to deliver antiviral agents, including, without limitation, fomivirsen sodium, foscarnet sodium, ganciclovir sodium, valganciclovir HCl, trifluridine, acyclovir, and famciclovir. The devices can be used to deliver local anesthetics, including, without limitation, tetracaine HCl, proparacaine HCl, proparacaine HCl and fluorescein sodium, benoxinate and fluorescein sodium, and benoxnate and fluorexon disodium. The devices can be used to deliver antifungal agents, including, for example, fluconazole, flucytosine, amphotericin B, itraconazole, and ketocaonazole.

The devices used to deliver analgesics including, without limitation, acetaminophen and codeine, acetaminophen and hydrocodone, acetaminophen, ketorolac, ibuprofen, and tramadol. The devices can be used to deliver vasoconstricors including, without limitation, ephedrine hydrochloride, naphazoline hydrochloride, phenylephrine hydrochloride, tetrahydrozoline hydrochloride, and oxymetazoline. Finally, the devices can be used to deliver vitamins, antioxidants, and nutraceuticals including, without limitation, vitamins A, D, and E, lutein, taurine, glutathione, zeaxanthin, fatty acids and the like.

The active agents delivered by the devices can be formulated to contain excipients including, without limitation, synthetic and natural polymers, including, for example, polyvinylalcohol, polyethyleneglycol, PAA (polyacrylic acid), hydroxymethyl cellulose, glycerine, hypromelos, polyvinylpyrrolidone, carbopol, propyleneglycol, hydroxypropyl guar, glucam-20, hydroxypropyl cellulose, sorbitol, dextrose, polysorbate, mannitol, dextran, modified polysaccharides and gums, phosolipids, and sulphobetains.

The invention will be clarified further by consideration of the following, non-limiting examples.

EXAMPLES

Example 1

A punctal plug known in the art was formed as follows. 1.50 g amount of epsilon polycaprolactone with an average $M_n$ of approximately 80,000 by GPC (available from Aldrich) was combined with 1.50 g EVA (EVATANE™, Arkema), and 3.00 g of bimatoprost (Cayman Chemicals), each with a purity of greater than approximately 97%. The mixture was then placed in a twin-screw micro-compounder Model No. 2000 from DACA Industries, Inc. that was fitted with a 0.25 mm die and compounded for 15 min. at 120 rpm and 65° C. Following compounding, the mixture was extruded into fibers at 75° C.

The fibers were cut into approximately 1.5 mm in length sections and inserted into the opening of Sharpoint ULTRA™ plug, available from Surgical Specialties. To insert the fiber, each plug was positioned under a stereomicroscope and tweezers were used to insert a fiber into the opening of each of the plugs. Each plug was then placed in a glass vial containing 1 cc of phosphate-buffered saline having a pH of 7.4. The vials were then placed into a water bath at 37° C. and gently agitated. Aliquots if 1 cc were collected at intervals of 3, 8 and 24 hours and then weekly for 3 weeks and analyzed for drug content via HPLC. In the graph in FIG. 4, the release is depicted as "Plug with Rod I".

Example 2

A first fiber was prepared by taking a 1.50 g amount of epsilon polycaprolactone with an average average $M_n$ of approximately 80,000 by GPC and combined with 1.50 g EVA and 3.00 g of bimatoprost (Cayman Chemicals), each with a purity of greater than approximately 97%. The mixture was then placed in a twin-screw micro-compounder that was fitted with a 0.25 mm die and compounded for 15 min. at 120 rpm and 65° C. Following compounding, the mixture was extruded into fibers at 75° C. and cut into rods of 0.75 mm in length.

A second fiber was prepared by taking 4.50 g amount of epsilon polycaprolactone with an average $M_n$ of approximately 42,000 by GPC and combined with 1.50 g of bimatoprost with a purity of greater than approximately 97%. The mixture was then placed in a twin-screw micro-compounder that was fitted with a 0.25 mm die and compounded for 15 min. at 120 rpm and 60° C. Following compounding, the mixture was extruded into fibers at 60° C. and cut into rods of 0.75 mm in length.

Figure 4:
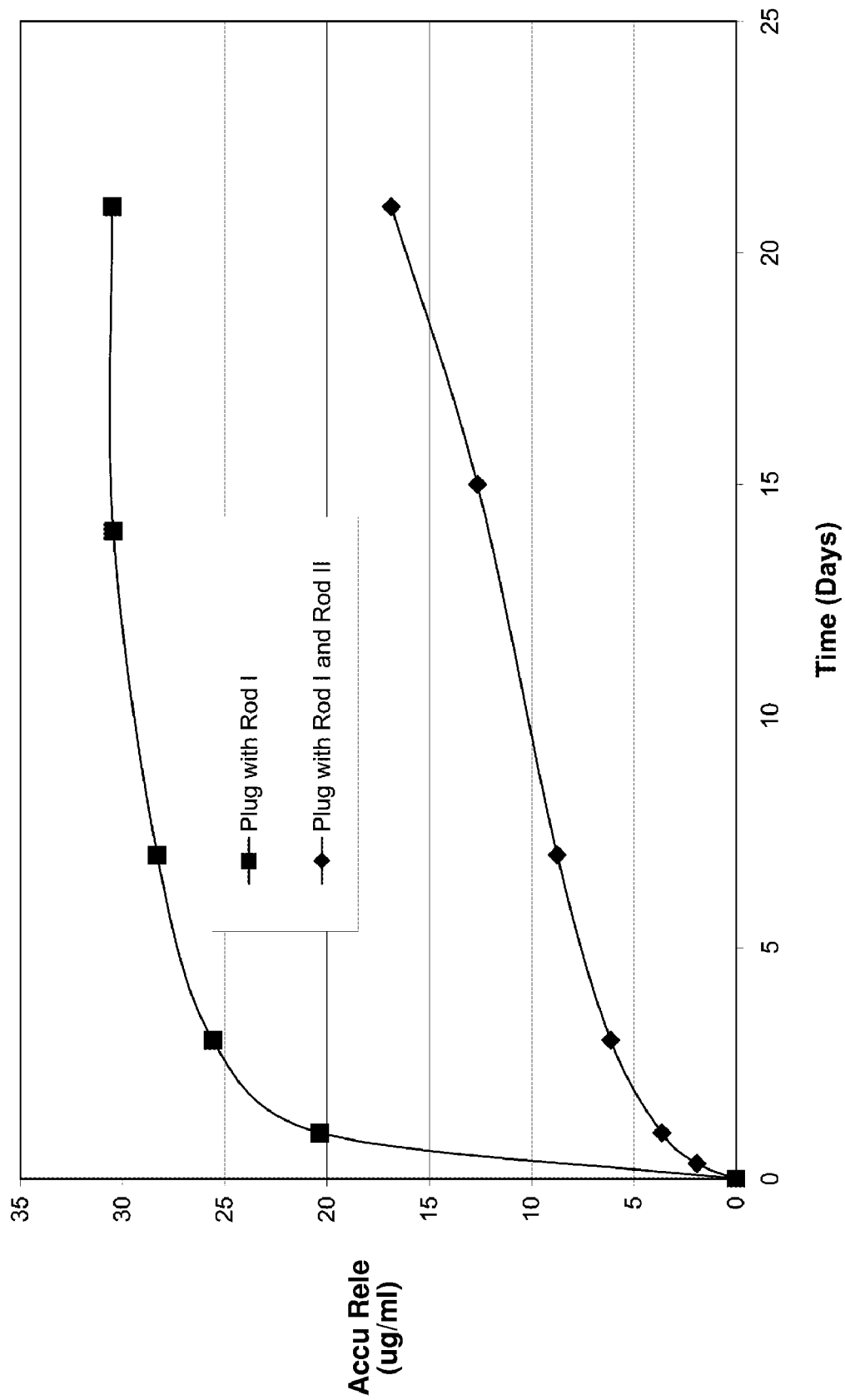
FIG. 4 is a graph of the active agent release over time.

One rod made from each of the first and second fibers was then inserted manually using tweezers into Sharpoint ULTRA™ plugs with the first fiber inserted first. The plugs were ten placed into glass vials with 1 cc of phosphate-buffered saline with a pH of 7.4. The vials were then placed into a water bath at 37° C. and gently agitated. Aliquots of 1 cc were collected at intervals of 3, 8 and 24 hours and then weekly for 3 weeks and analyzed for drug content via HPLC. In the graph of FIG. 4 the release is depicted as "Plug with Rod I and II". As shown by a review of the data in the graph, the release profile is better in that it is a slower, linear release profile as compared of the plug of Example 1.

Example 3

Figure 5:
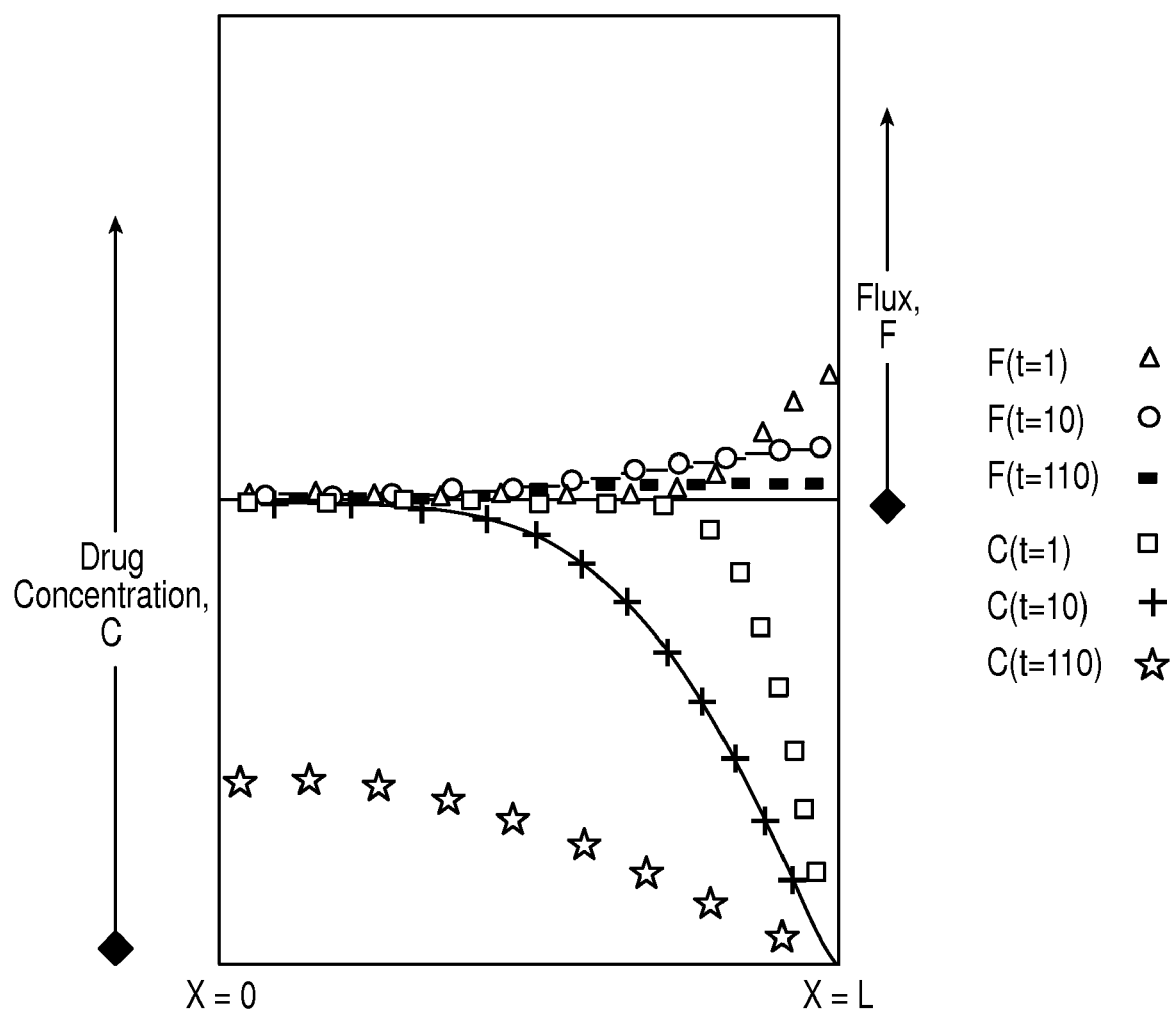
FIG. 5 is a graph of concentration and flux for a uniform concentration.

In FIG. 5 is depicted the time course for spatial drug concentrations and fluxes along the axis of a one-dimensional matrix, meaning a single active agent-containing fiber that has no gradient. The calculations were performed using MIT 3.091 Diffusion Simulation software available at http://web.mit.edu/course/3/3.091/www/diffusion/. The model non-dimensionalizes length scales, permeability concentration and time and, thus, specific release curves for specific materials, drugs, and time scales were not calculated. By looking at the relative value of surface flux as a function of time and varying initial drug loading profiles, one can track the relative burst release and overall qualitative release kinetic profile (i.e., zero-order versus first-order versus second-order) regardless of material permeability or surface area.

A series of 6 time points are shown with corresponding profiles in the matrix. Three of the points are flux, F(t, x), as a function of time and position along the fiber. Along the graph's x axis x=L denotes the release surface and x=0 denotes the opposite end of the fiber. An additional three points are concentration, C(t, x), as a function of time and position along the fiber.

In the fiber of the example, there is completely uniform drug-loading. The flux at the release surface is equivalent to an instantaneous drug release rate. In the figure is also depicted a significant burst release effect meaning large flux values at the release surface persisting for significant times, which is typically observed with commonly used uniform drug-loaded matrices. About 25% of the total drug load is released during this burst phase. The initial release rate at t=1 compared to the intermediate release rate at t=0 provides a relative burst factor calculated as:

$$\frac{F_{(t=1, x=L)}}{F_{(t=10, x=L)}}$$

The value for the single rod is approximately 2.3.

Example 4

Figure 6:
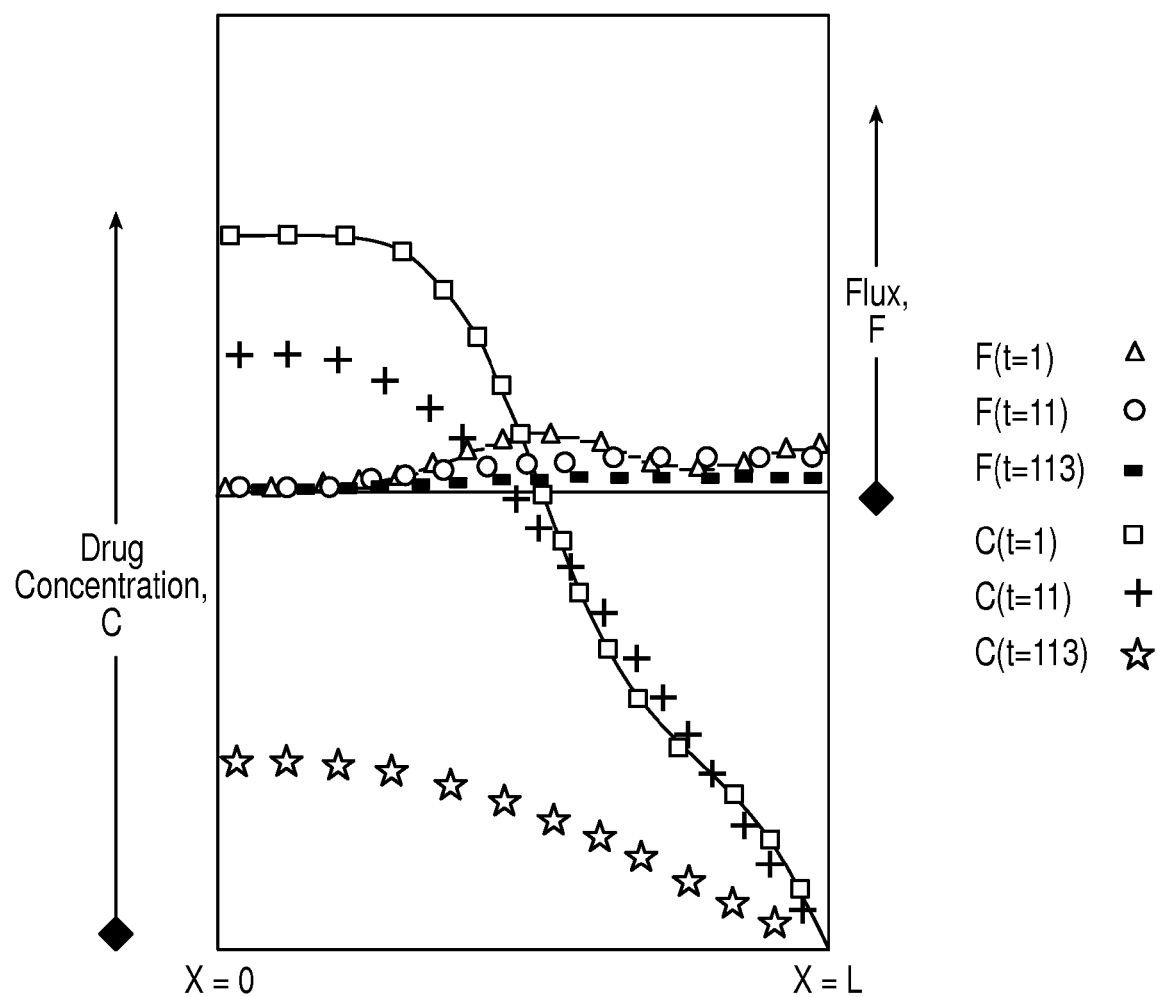
FIG. 6 is a graph of concentration and flux for a punctal plug with two fibers.

In FIG. 6 is depicted release profiles for a punctal plug with two fibers of equal length, the outermost fiber having an initial active agent load concentration that is 25% of that of the other fiber. As seen in FIG. 6, a significant reduction in the initial release is shown. The burst release of the active agent is <10% and the relative burst factor $$\frac{F_{(t=1,x=L)}}{F_{(t=11,x=L)}}$$

is approximately 1.2.

Example 5

Figure 7:
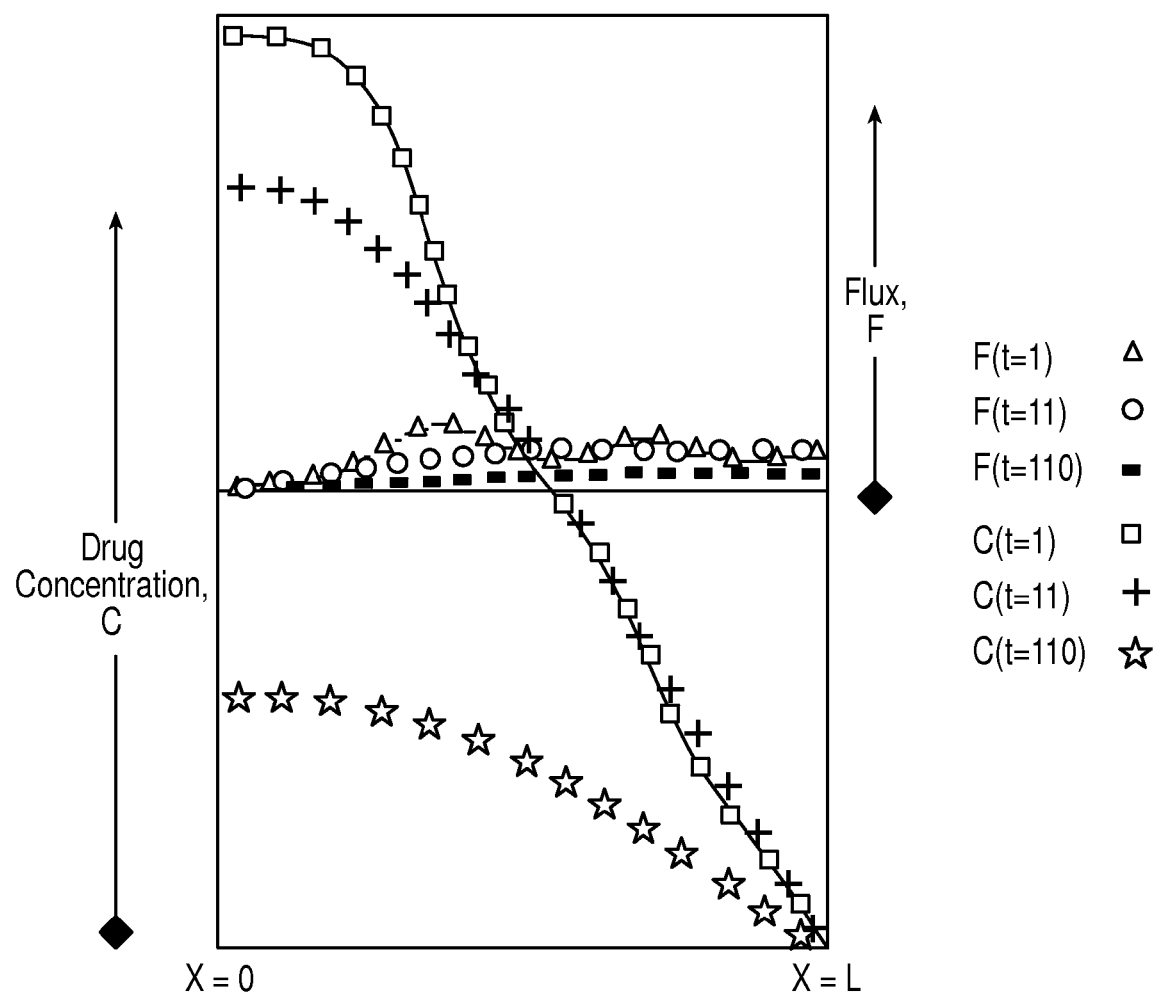
FIG. 7 is a graph of concentration and flux for a punctal plug with three fibers.

In FIG. 7 are shown release profiles for the same points along three rods of equal length wherein the initial ratio of active agent loading concentration is 8:4:1 for the inner, middle and outer fibers, respectively. The burst release of the active agent is <5% and the relative burst factor $$\frac{F_{(t=1,x=L)}}{F_{(t=11,x=L)}}$$

is approximately 1.0.

Example 6

Formulation Masterbatch Compounding:

A bimatoprost formulation masterbatch was formed by combining 2.20 g of epsilon polycaprolactone (PCL) with an average $M_n$ of approximately 80,000 by GPC (available from Aldrich) with 2.2 g EVA (EVATANE™ 3325, Arkema), and 0.4 g of bimatoprost (Johnson Matthey Pharma Services), each with a purity of greater than approximately 97%. The mixture was then placed in a ThermoFisher Minilab II microcompounder and compounded for 15 min. at 30 rpm and 66° C. Following compounding, the mixture was recovered and placed in a 1 CC disposable polycarbonate syringe, annealed at 66° C., then allowed to cool and solidify.

Figure 8:
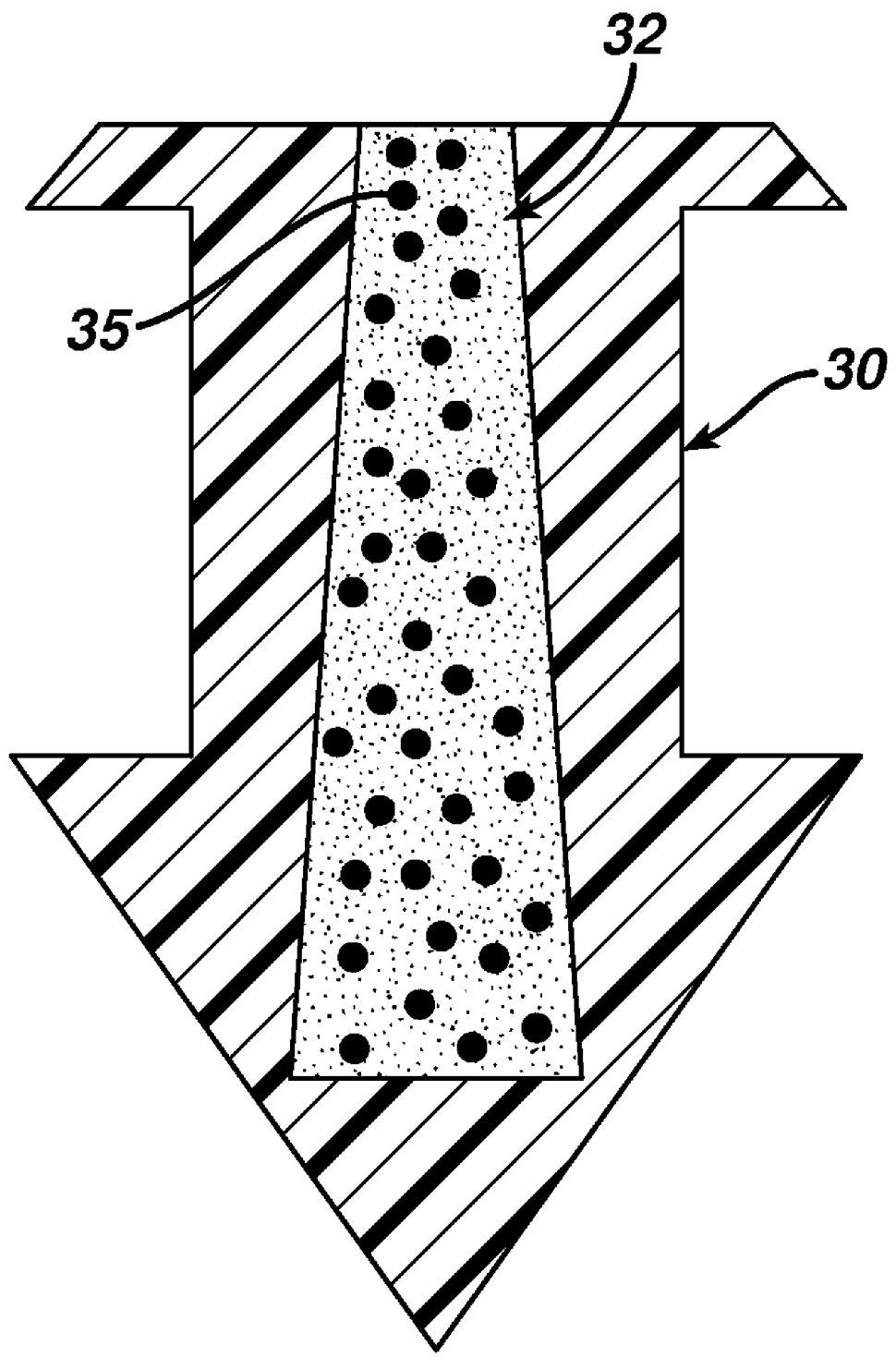
FIG. 8 is a fourth embodiment of the invention.

Tapered-Reservoir Punctal Plugs and Comparators:

A punctal plug with a tapered reservoir was designed and produced and compared to those having a straight cylindrical central reservoir (for example, Sharpoint ULTRA™ plug, available from Surgical Specialties, Inc.) This tapered plug is substantially as shown in FIG. 8. Those used in this example had a tapered central reservoir of approximately 1.6 mm in length and a circular cross-sectional diameter that tapers from about 0.4 mm ID at the end distal to the reservoir opening to about 0.2 mm ID at the reservoir opening. Externally, they had an overall plug length of about 1.92 mm, a central shaft OD of about 0.7 mm, a collar proximal to the reservoir opening having a diameter of about 1.19 mm, and an arrow-head tip of about 1.2 mm OD at its widest point. The tapered plugs were translated into a mold and manufactured by Kipe Molds, Inc (Placentia, Calif.) using commercial liquid silicone injection-molding. The liquid silicone elastomer was a thermoset material of nominal durometer of about 60 Shore A on an Arburg injection-molding machine at about 160° C.

Plugs were also made having a straight cylindrical reservoir of about 0.4 mm ID, and comparable external dimensions to the tapered reservoir plug, was also produced at Kipe Molds, Inc. Additionally, Sharpoint ULTRA™ plugs commercially available from Surgical Specialties, Inc. were used. These had a straight cylindrical internal reservoir of about 0.2 mm ID, and exterior dimensions comparable to the tapered plug.

Reservoir Filling Process:

Filling the active agent core material into a non-cylindrical punctal plug reservoir and achieving a final active agent core possessing a conforming non-cyldrincal shape was accomplished by dispensing the formulation from the 1 CC polycarbonate syringe into the tapered punctal plug as a melt. A syringe pump, heated dispensing tip, and control software were fashioned to dispense the formulation at 66° C. into tapered punctal plug cavities held on a heated X-Y positioning stage. Tapered punctal plugs filled with bimatoprost formulation were allowed to cool and solidify.

Plugs with straight cylindrical cavities comprising a 0.2 mm ID reservoir and plugs comprising a 0.4 mm ID reservoir were filled with the same formulation batch under comparable melt dispensing conditions as the tapered-reservoir plugs.

Tapered-Reservoir Punctal Plug Dissolution Testing:

Each plug was placed in a glass vial containing 1 cc of phosphate-buffered saline having a pH of 7.4. The vials were then placed into an incubator at 37° C. and gently agitated. Aliquots of 1 cc were collected and replaced at intervals of 0.33, 1, 3, 7 days, and then weekly for 7 weeks and analyzed for bimatoprost content via HPLC. The active agent released at each time point was then analyzed in terms of the active agent release rate, in micrograms per day, as a function of time.

Results:

The amount of formulation protruding from the open end of the punctal plug reservoir was not, on average, different between the tapered plugs and the straight cylinder plugs. (increased protrusion of active agent core can otherwise increase the amount of initial "burst" of active agent release)

Figure 9:
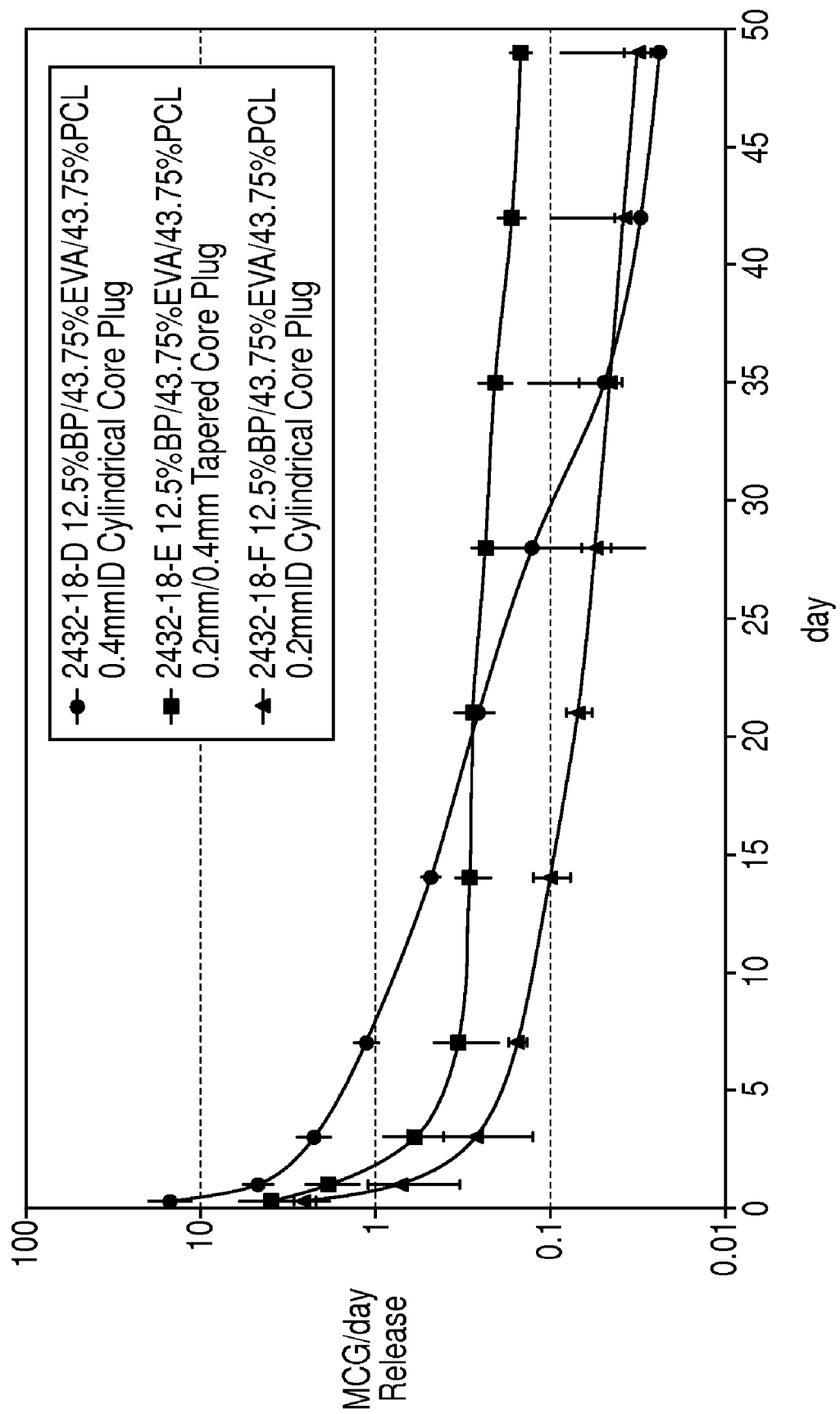
FIG. 9 is a graph of concentration and flux for a punctal plug as in FIG. 8.

The plugs with 0.2 mm ID cylindrical reservoir and 0.4 mm ID cylindrical reservoir differ by 2-fold in reservoir diameter, equating to a 4-fold difference in formulation volume and mass in the reservoir. As depicted in FIG. 9, both release rate curves have a similar overall shape, with a significant initial burst release of active agent followed by a continual decline in release rate over time.

Conversely, the tapered-reservoir plugs contain half as much active agent formulation as the 0.4 mm ID cylindrical-reservoir punctal plug yet twice that of the 0.2 mm ID cylindrical-reservoir plug. However, as depicted in FIG. 9, the tapered-reservoir plug's active agent release rate curve is distinct from the plugs having straight cylinder designs with the tapered plugs curves being flatter and more extended. The initial rate of active agent release, being about 4 mcg/day, is much smaller than that of the 0.4 mm ID plug, being about 15 mcg/day, and is comparable to the 0.2 mm cylindrical plug, being about 3 mcg/day. Yet, the tapered-reservoir plug affords a larger and more consistent post-burst release rate of active agent than the 0.2 mm cylindrical-reservoir plug over the duration of study, about 0.2 to 0.3 mcg/day versus about 0.03 to 0.1 mcg/day. Beyond day 21, the tapered-reservoir release rate also greatly exceeds the release rate of the larger 0.4 mm cylindrical reservoir plug, which has fallen to less than 0.1 mcg/day.

The gradient of cross-sectional area along the axis of the tapered reservoir affords a more extended and consistent delivery of active agent than either cylindrical reservoir comparator achieves using the same formulation masterbatch.

This result will translate to a variety of stepwise or continuous gradients in cross-sectional area available for diffusion of active agent within the reservoir. As with the reservoirs comprising spatial gradients of active agent disclosed herein, the stepwise or continuous gradients disclosed herein can reduce potentially intolerable initial burst release of active agent from a punctal plug whilst delivering efficacious rates of active agent to the ocular tissues for a longer period of time.

What is claimed is:

1. A method for delivering medication to the eye, comprising:
providing an ophthalmic device, comprising: a body having a first end and a second end; a surface extending between the two ends; a reservoir contained within the body wherein the reservoir comprises at least one opening, an active agent-containing material and an active agent, wherein the active agent is present in a discontinuous concentration gradient within the active agent-containing material;
inserting the ophthalmic device in a lacrimal punctum; and
releasing the active-agent in a pulsatile manner with respect to time.

2. The method of claim 1, wherein the device is a punctal plug.

3. The method of claim 2, wherein the active agent-containing material comprises poly(epsilon-caprolactone) and ethylene vinyl acetate.

4. The method of claim 3, wherein the poly(epsilon-caprolactone) and ethylene vinyl acetate are each present in an amount of about 50 weight percent.

5. The method of claim 1 or 3, wherein the active agent-containing material is in a form of one or more fiber or fiber-like structures.

6. The method of claim 1 or 2, wherein the device further comprises a release modulating component selected from the group consisting of biodegradable semi-permeable membranes, non-biodegradable semi-permeable membranes, pores and combinations thereof.

7. The method of claim 1 or 2, wherein the active-agent containing material further comprises an outer segment comprising a first material having a low concentration of the active agent and an inner segment comprising a second material having a high concentration of the active agent, wherein the permeability of the first material to the active agent is less than the permeability of the second material.

8. The method of claim 1, 2, or 3, wherein the active agent-containing material further comprises one or more of a phase separated inclusion, a destabilizing inclusion or a stabilizing inclusion.

9. A method for delivering medication to the eye, comprising:
providing an ophthalmic device, comprising: a body having a first end and a second end; a surface extending between the two ends; a tapered reservoir contained within the body wherein the reservoir comprises at least one opening, an active agent-containing material and an active agent, wherein the active agent is present in a discontinuous concentration gradient within the active agent-containing material;
inserting the ophthalmic device in a lacrimal punctum; and
releasing the active-agent in a pulsatile manner with respect to time.

10. The method of claim 9, wherein the device is a punctal plug.

11. The method of claim 10, wherein the active agent-containing material comprises poly(epsilon-caprolactone) and ethylene vinyl acetate.

12. The method of claim 10, wherein the poly(epsilon-caprolactone) and ethylene vinyl acetate are each present in an amount of about 50 weight percent.

13. The method of claim 10, wherein the active agent-containing material is in a form of one or more fiber or fiber-like structures.

14. The method of claim 9, wherein the device further comprises a release modulating component selected from the group consisting of biodegradable semi-permeable membranes, non-biodegradable semi-permeable membranes, pores and combinations thereof.

15. The method of claim 9, wherein the active-agent containing material further comprises an outer segment comprising a first material having a low concentration of the active agent and an inner segment comprising a second material having a high concentration of the active agent, wherein the permeability of the first material to the active agent is less than the permeability of the second material.

16. The method of claim 9, wherein the active agent-containing material further comprises one or more of a phase separated inclusion, a destabilizing inclusion or a stabilizing inclusion.

* * * * *